(12) United States Patent
Lacout et al.

(10) Patent No.: US 6,521,264 B1
(45) Date of Patent: Feb. 18, 2003

(54) METHOD FOR PREPARING A BIOMATERIAL BASED ON HYDROXYAPATITE, RESULTING BIOMATERIAL AND SURGICAL OR DENTAL USE

(75) Inventors: Jean-Louis Lacout, Toulouse (FR); Zinèb Hatim, Casablanca (MA); Michele Frache-Botton, Fonsegrives (FR)

(73) Assignee: Teknimed, Vic en Bigorre Cedex (FR)

( * ) Notice: Subject to any disclaimer, the term of this patent is extended or adjusted under 35 U.S.C. 154(b) by 0 days.

(21) Appl. No.: 09/424,313

(22) PCT Filed: Mar. 17, 1999

(86) PCT No.: PCT/FR99/00595
§ 371 (c)(1),
(2), (4) Date: Nov. 22, 1999

(87) PCT Pub. No.: WO99/48809
PCT Pub. Date: Sep. 30, 1999

(30) Foreign Application Priority Data

Mar. 20, 1998 (FR) ............................................. 98 03459

(51) Int. Cl.$^7$ .......................... A61K 6/033; A61K 9/00; A61K 33/06; A61K 33/42; A61B 17/56; A61F 2/28; C01B 25/32; C04B 12/02

(52) U.S. Cl. ...................... 424/602; 424/601; 424/604; 424/605; 424/606; 424/57; 424/422; 424/423; 424/426; 514/54; 514/55; 514/75; 514/129; 514/143; 514/557; 423/305; 423/307; 423/311; 423/315; 106/35; 106/690; 106/691; 606/76; 606/77; 433/228.1; 427/2.26; 427/2.27

(58) Field of Search ................................ 424/601, 602, 424/423, 400, 604–606, 57, 422, 426; 514/75, 54, 55, 129, 143, 557; 423/305, 307, 311, 315; 106/35, 690, 691; 606/76, 77; 433/228.1; 427/2.26, 2.27

(56) References Cited

U.S. PATENT DOCUMENTS

| | | | | |
|---|---|---|---|---|
| RE33,161 E | * | 2/1990 | Brown et al. .................. | 106/35 |
| RE33,221 E | * | 5/1990 | Brown et al. .................. | 106/35 |
| 5,522,893 A | * | 6/1996 | Chow et al. .................. | 106/35 |
| 5,605,713 A | * | 2/1997 | Boltong ........................ | 106/35 |
| 5,954,867 A | * | 9/1999 | Chow et al. .................. | 106/35 |

FOREIGN PATENT DOCUMENTS

| | | |
|---|---|---|
| EP | 0 323 632 | 7/1989 |
| EP | 0 416 761 | 3/1991 |
| FR | 2 693 716 | 1/1994 |
| FR | 2805747 | * 9/2001 |
| WO | WO 95/08319 | 3/1995 |

OTHER PUBLICATIONS

Derwent Abstract, accession No. 2001–618733, abstracting: FR 2805747 (Sep. 2001).*

* cited by examiner

Primary Examiner—John Pak
(74) Attorney, Agent, or Firm—Young & Thompson

(57) ABSTRACT

A solid powder product with a Ca/P ratio of between 1.40 and 1.90 is prepared from tricalcium phosphate and tetracalcium phosphate. An aqueous solution containing calcium ions and phosphate ions with a Ca/P ratio higher than 0.20 and lower than 0.50 is prepared. The aqueous solution and the solid powder product and optionally water are mixed to obtain a mixture with a liquid/solid weight ratio of between 0.30 and 0.65 and a resulting paste with a Ca/P ratio of between 1.50 and 1.67.

15 Claims, No Drawings

METHOD FOR PREPARING A BIOMATERIAL BASED ON HYDROXYAPATITE, RESULTING BIOMATERIAL AND SURGICAL OR DENTAL USE

This application is a 371 of PCT/FR99/00595, filed on Mar. 17, 1999.

FIELD OF THE INVENTION

The invention relates to a process for the production of a biomaterial essentially constituted of phosphocalcium hydroxyapatite of an atomic ratio of Ca/P comprised between 1.50 and 1.67. The invention relates to the obtained biomaterial and to uses of the latter, in particular for dental or bone filling or restoration. The invention also relates to surgical or dental set for practicing this invention.

BACKGROUND OF THE INVENTION

Phosphocalcium hydroxyapatites are well known and more and more used in the surgical or dental field because of their properties of biocompatibility and osteoconduction. They can be used in the dental field for periodontal filling, restoration of bone crests, filling cysts or recesses after dental extraction . . . and, in orthopedic surgery, for filling bone defects, interstitial filling between prosthesis and cortical bone, injection into vertebral bodies . . . The material thus emplaced can if desired contain active substances which, after hardening in situ of the material, are slowly diffused.

The preparation of phosphocalcium hydroxyapatites is essentially carried out according to two different ways each leading to specific applications:

- on the one hand, an in situ preparation, in which the hardening of the hydroxyapatite is effected on the site of use at low temperature (in particular in vivo at body temperature), this preparation permitting the practice of the mentioned surgical or dental applications (this preparation which has a hardening phase at the site of utilization is designated hereafter as "preparation in situ" even if certain phases can be carried out apart from the utilization site),
- on the other hand, an industrial preparation producing either pulverulent apatites or slightly bonded ones having limited mechanical properties, or ceramic apatites after high temperature thermal treatment or compression treatment in the presence of a binder.

The industrial apatites described above, which have good mechanical properties, are of course useless in applications in which a surgical or a bone operating site of any type must be filled or restored, because they require, to obtain their hardening, an industrial treatment under severe conditions. Moreover, industrial calcine apatites are always stoichiometric and have a low specific surface (less than 10 m$^2$/g) and low solubility (solubility product equal to 10$^{-119}$): these properties render the material difficultly bioresorbable, which represents a drawback in most of the surgical or dental applications (in which a slow replacement by bone of the implanted material is generally sought).

The present invention relates to apatites "prepared in situ", that is whose hardening can be carried out at low temperature in situ at the utilization site. Of course, these apatites can, as the case may be, be used in other applications such as those of industrial apatites.

Known apatites for in situ preparation are generally prepared as cements by mixing with water a powder containing one or more calcium phosphates selected from known phosphates: monocalcium phosphate hydrated or not, dicalcium phosphate hydrated or not, tricalcium phosphate α or β, tetracalcium phosphate (U.S. Pat. No. 461,053, EP 0 416 761, FR 2.693.716 . . . ). Certain authors have proposed first dissolving in water for mixing monocalcium phosphate so as to avoid untimely hydration of this phosphate in the powder (WO 95/083149). The apatites obtained by these known methods have essentially major drawbacks. In the first place, their mechanical properties are mediocre (compressive resistance of the order of 5 to 8 Megapascals), which, in numerous cases, is a major drawback (periodontal filling, injection in vertebral bodies, interstitial filling for sealing prostheses, osteotomy wedges hardened in situ . . . ).

Moreover, there is often seen with these known products the formation of "lumps", of non-reproducible setup times, and an exfoliation of the material after its in vivo emplacement because of the biological liquids present; certain faults lead either to grave difficulties for emplacement, or to a mediocre quality of the obtained implant (bad filling, bad adherence at the operating site), or a very troublesome production of exfoliated particles outside the operating site. This is particularly serious in surgery and leads many surgeons to reject this type of product after one or more unfortunate experiences.

SUMMARY OF THE INVENTION

The present invention provides a process for the in situ preparation of an apatite biomaterial, having good reproducibility and more certain and easy use than the known processes (homogeneity of the product, constant setup time, ease of shaping and modeling, absence of exfoliation).

Another object is to permit obtaining a biomaterial having improved mechanical properties relative to the known apatite materials prepared in situ.

Another object is to permit obtaining a biomaterial having a solubility and a specific surface significantly greater than the existing apatite biomaterials.

An object of the invention is in particularly to provide an apatite material which combines excellent properties of resistance to compression, good solubility in life media and a high specific surface.

To this end, the process contemplated by the invention for preparing a biomaterial whose hardening takes place at the site of utilization, in particular cold on a surgical or dental operating site (temperature below about 40° C.), is of the type in which are mixed calcium phosphates to obtain a hydroxy apatite within an atomic ratio Ca/P comprised between 1.50 and 1.67; the process of the invention is characterized in that:

a) there is first prepared a solid pulverulent product from a tricalcium phosphate powder and from a tetracalcium phosphate powder by mixing said powders so that the atomic ratio Ca/P of the obtained product will be substantially comprised between 1.40 and 1.90, b) there is prepared an aqueous solution or aqueous solutions to mix with said solid pulverulent product, said solution or solutions containing calcium ions and phosphate ions such that the overall atomic ratio Ca/P of the solutions will be greater than 0.20 and that the atomic ratio Ca/P of each solution will be less than 0.50, c) the aqueous solution or solutions and the solid pulverulent product are mixed, with the addition of water as the case may be, such that the liquid/solid weight ratio of the final mixture obtained will be comprised between 0.30 and 0.65 so as to obtain a homogeneous paste of an atomic ratio Ca/P comprised between 1.50 and 1.67, said paste being emplaced at the utilization site for its hardening in situ.

Experience has shown that this preparation from, on the one hand, a solid pulverulent product containing tricalcium phosphate and tetracalcium phosphate, on the other hand, from an aqueous solution containing calcium ions and phosphate ions, results in obtaining a naturally homogeneous pasty mixture having no tendency to lump, and having progressive and regular setting up and a constant setup time (for a given composition), with the four-fold condition that:

- The Ca/P ratio of the solid pulverulent product be comprised in the above-indicated range (preferably between 1.70 and 1.85),
- The Ca/P ratio of the solution or of each solution if several solutions are used, will be less than 0.50 (preferably less than 0.40),
- The Ca/P ratio of the solution, or the overall Ca/P ratio of the assembly of the solutions if several solutions are used, be greater than 0.20 (preferably greater than 0.35),
- The liquid/solid weight ratio of the produced mixture is comprised between 0.30 and 0.65.

The malleable pasty mixture thus obtained is deposited at the utilization site at which it undergoes setting and at which it then proceeds to harden. The utilization site can be a surgical or dental operating site and the setting up and hardening take place at body temperature (temperature below 40° C.). The site can also be a mold to produce a piece, the setting up and hardening being accomplished cold or at low temperature (particular below 90° C.) so as to increase the speed of hardening. The duration of setting can vary between 10 and 45 minutes as a function of the composition in the above-identified ranges. The hardening leading to final properties of the biomaterial is obtained at the end of a period of two to four hours at body temperature and several hours at a temperature comprised between 60° C. and 100° C. Analyses of the obtained biomaterial have shown that the latter is essentially constituted by a microcrystalline hydroxy apatite of atomic ratio Ca/P comprised between 1.50 and 1.67, having in combination the following characteristics:

- compressive resistance substantially comprised between 15 and 25 Megapascals,
- solubility corresponding to a solubility product comprised between $10^{-94}$ and $10^{-100}$,
- and a specific surface substantially comprised between 20 and 120 $m^2/g$.

Compressive tests were carried out on cements shaped with "Plexiglas" molds 6 mm in diameter and 6 mm high. After shaping, the molds are placed in deionized water at 37° C. After 24 hours, the cements are demolded then kept under the same conditions (water at 37° C.). Tests were carried out at the end of 26 days of maturing. Before the compressive tests, the specimens were dried. The compressive test is carried out by subjecting the cylindrical specimen to two opposite coaxial forces by placing it between the plates of a press. The specimen is subjected to a uniaxial stress which is supplied at a constant speed of 0.5 mm/min. An associated software permits tracing directly the stress as a function of the amount of deformation. Rupture is determined by an abrupt change in the shape of the curve.

Solubility is determined by suspending in demineralized and decarbonated water (100 ml) a predetermined quantity of cement (50 mg) of a granulometry comprised between 20 and 50 microns. The suspension is agitated several times per day for 30 days. At the end of this period, the pH is measured and sampling is carried out to determined by ICPMS the phosphorus and the calcium. The solubility product can then be determined by computation.

Measurement of the specific surface is carried out by an analyzer of the "Micrometrics Flow Sorb II 2300", on a specimen of crushed cement.

No known apatite material combines all of these properties which can be essential in a large number of applications, in particular surgery and dentistry. Moreover, this material has a microporosity of the order of 30% to 55%, which is remarkable, given its mechanical properties. This porosity (known per se) permits the circulation of biological fluids in in vivo uses, which promotes the biointegration of the biomaterial and its bioresorbability over time.

It appears that the mentioned advantages of the process and the properties of the obtained biomaterial result from the intermediate formation, during mixing and setting up, of grains of large constant size, which, upon their evolution to apatite, lead to a morphology of large regular interlock needles. This interlocking of needles gives the mechanical properties, the porosity and the surface properties.

So as to facilitate the work of the practitioner, in particular in surgical and dental applications, the solid pulverulent product and the aqueous solution are prepared batchwise in separate contains such that the overall liquid/solid weight proportion will be comprised between 0.30 and 0.65 and that the overall atomic ratio Ca/P will be comprised between 1.50 and 1.67. It suffices for the practitioner to mix the batches homogeneously without the addition of water, to obtain a paste ready to use at the utilization site; preferably, the liquid batch will be mixed with the solid batch as required by the mixture.

The solid pulverulent solid is preferably first treated so that the mean diameter of the grains $D_{50}$ will be comprised between 15 and 20 microns and that its cross-sectional diameter $D_{95}$ will be equal to 100 microns. There is thus avoided the presence of large size grains which could promote the formation of lumps; moreover, such a narrow granulometric distribution (homogenous fine grains) contributes to the production of a progressive and regular setting up, which is perfectly reproducible.

DETAILED DESCRIPTION OF THE INVENTION

According to a preferred embodiment, there is prepared the solid pulverulent product by mixing a powder of α tricalcium phosphate and a powder of tetracalcium phosphate. By powder of α tricalcium phosphate is meant a powder containing at least 85% of phosphate of this form. The α tricalcium phosphate is much more soluble than the β form and leads to a very uniform and greater setting up and to the obtention of a paste of improved homogeneity.

Moreover, the aqueous solution is preferably prepared by mixing phosphoric acid and water with calcium hydroxide and/or calcium carbonate. The use of these species avoids the presence of counter ions in the obtained product and leads to the obtention of an apatite of high purity (it is to be noted that, in acid medium, the carbonate is eliminated in the form of $CO_2$). The use of calcium carbonate leads to a solution having a pH of the order of 2.25, higher than if the calcium is supplied by hydroxide (pH of the solution of the order of 1.75). The setting up is slower in the first case. As the case may be, the mixture of hydroxide and carbonate can be used to adjust the setup time to a desired value. This setup time can also be adjusted by the addition of small quantities of acid suitable to lower the pH of the solution without however reaching a value equal to or below 1 (a tendency to lumping appears below this value).

It is possible to add to the solid pulverulent product and/or to the aqueous solution, other additives adapted further to increase the regularity of setting up of the paste. For example, glycerophosphate, particularly sodium, potassium or calcium glycerophosphate, can be added such that the weight percent of this compound relative to the final mixture will be below 15%. This composition contributes to an improvement of the regularity of setting up and slightly decreases the speed of setting up. In the case of calcium glycerophosphate, account must be taken of the ratio of calcium due to the addition of this compound to prepare and test initial products (pulverulent solid product, aqueous solution) so as to obtain a final atomic ratio Ca/P comprised within the mentioned range. The calcium surplus from the calcium glycerophosphate can in particular be compensated by suitable addition of phosphoric acid into the solution: this leads to a lowering of the pH of the solution and to a reduction of the setup time, which may be desirable in certain applications.

There can also be added to the solid pulverulent product and to the aqueous solution, lactic acid, such that the weight percent of this compound relative to the final mixture will be below 4%. This compound has a double effect: an immediate effect consisting in slowing the crystallization of the mixture and increasing the regularity of setting and increasing the duration of the latter, and a final effect during hardening arising from the formation of lactate and producing a material of increased hardness.

It is also possible to add to the solid pulverulent product and/or to the aqueous solution, an alginate or a guar gum, or chitosan, such that the weight percent of the compound relative to the final mixture will be less than 2%. These compounds increase the setup time and permit, as the case may be, adapting the latter to a suitable value. Moreover, they give the obtained mixture Theological properties of sliding, rendering the mixture adept to circulate in conduits or passages particularly for its injection at the utilization site. Moreover, chitosan influences the chemical and crystallographic evolution of the paste obtained by stabilizing a portion of the latter at a preapatitic stage: there is thus obtained a crystalline biomaterial very near to that of bone, having a higher resorbability.

Moreover, the combination of the properties of microporosity of the obtained material and resorbability of the latter in vivo render said material well adapted to be loaded with an active substance so as to ensure its in situ release, by diffusion and the resorption effect of the material. Such an active substance added to the solid pulverulent property in a quantity sufficient to obtain the desired result, can in particular be constituted by an antibiotic, an antimitotic (particularly for material adapted to fill a cancerous tumor), or a growth factor (particularly in the case of filling bones so as to accelerate the regeneration of the bone).

The process of the invention is particularly well adapted for the production of a filling or a restoration at a dental or surgical site. The mixture of the aqueous solution and/or the solid pulverulent product is produced at ambient temperature, and the obtained paste is then emplaced in the dental or bone site so as to ensure its hardening at 37° C. The solid pulverulent product and the aqueous solution are then prepared in a batch as already indicated and loaded into two closed sterilized containers. One of the additives defined above can be added to said batches, in particular sodium, potassium or calcium glycerophosphate, to the solid pulverulent product.

According to an embodiment suitable for surgical uses, the surgical set available to the surgeon comprises:
(a) for a set of a mean weight of 20 g:
    a batch of solid pulverulent product containing between 4.20 and 4.50 g of α tricalcium phosphate, between 5.50 and 5.80 g of tetracalcium phosphate, and as the case may be between 1.4 and 1.6 g of sodium, potassium or calcium glycerophosphate,
    a batch of aqueous solution containing between 0.18 and 0.22 g of calcium hydroxide and between 1.30 and 1.50 g of phosphoric acid in solution between 3.8 and 4.2 g of water.
(b) for a set of mean weight of 40 g: batches equal to twice the above batches,
(c) for a set of mean weight of 80 g: batches equal to four times the above batches (a).

Such a surgical set permits in particular the surgeon to carry out interventions under the best conditions: filling of bone defects, refection of the tibial plateau, additive osteotomy, sealing prostheses, refection of the cotyle base, and in most cases, grafting by means of the material avoiding the need for autological graft.

According to another embodiment suitable for dental applications, the set comprises:
(a) for a set of mean weight of 1.5 g:
    a batch of solid pulverulent product containing between 0.42 and 0.45 g of α tricalcium phosphate, between 0.55 and 0.58 g of tetracalcium phosphate, and as the case may be, between 0.14 and 0.6 g of sodium, potassium or calcium glycerophosphate,
    a batch of aqueous solution containing between 0.02 and 0.025 g of calcium hydroxide and between 0.13 and 0.15 g of phosphoric acid in solution in 0.3 to 0.4 g of water.
(b) for a set of mean weight of 3 g: batches equal to twice the above batches.

Such a dental set permits in particular a practitioner to carry out interventions under the best conditions: filling of periodontal pockets, filling gaps, rebuilding ridges . . .

The following examples illustrate the process of the invention and the properties of the obtained biomaterial, the ratio L/S indicated in these examples corresponds to the liquid/solid weight ratio of the pasty mixture, designated cement, before hardening.

EXAMPLE 1

Preparation of a Cement Ca/P=1.67; L/S=0.45; NaGP=0%

The preparation in question corresponds to a preparation for a final quantity of 145 g.

a) There is first prepared a mixture of powder by exact weight, comprising the following constituents:

Tetracalcium phosphate=62.38 g (tetracalcium phosphate is first crushed such that its granulometry will be less than 70 microns).

α tricalcium phosphates=37.62 g.

The calcium/phosphate atomic ratio of this mixture is equal to 1.79.

This mixture is carefully homogenized by means of a powder mixture.

There is then prepared a solution in the following manner:

b) There are measured 6.1 g of concentrated phosphoric acid (d=1.69); there is slowly added 1.46 g of calcium hydroxide. It is then completed with 45 ml of distilled water. There is thus obtained an initial clear solution, stable, of a calcium/phosphorus atomic ratio Ca/P=0.377.

c) The powder mixture is poured into a small mortar. All of the solution is then added while vigorously stirring with a pestle or a spatula. The mixture is initially granular but becomes very quickly smooth and homogeneous. After about one to two minutes of mixing, the mixture is left to stand. After about 10 minutes it has a consistency such that it can be molded and emplaced. It completes its setup after about 15 minutes.

The cement prepared according to this method has an overall atomic ratio Ca/P=1.67 and a liquid/solid ratio L/S=0.45.

If it is desired to examine the progress of this cement in vitro, it is necessary to observe the hardening of the cement in a humid medium (analogous to that encountered in a biological medium).

The development of the cement from a crystallographic point of view, can be followed by x-ray detraction. There is observed the progressive disappearance of the initial phases of the mixture and the formation after about 72 hours of an apatitic phase moderately crystallized; this phase is analogous to that of the mineral portion of the bone.

Throughout the development of the mixture, the modifications of the plasticity can be measured by using a penetrometer: the latter measures the resistance to penetration at the surface of the cement of a 1 mm$^2$ point. It is considered that a value of about 250 g/mm$^2$ corresponds to the limit for emplacing the cement at the utilization site. At a value corresponding to 300 g/mm$^2$, the cement has lost all malleability: it is totally set up. Of course, then it continues its hardening.

In the case of the cement described here, the limit value (250 g/mm$^2$) is reached after 15 minutes. The resistance to compression is 15 MPa. Its porosity is 41%.

EXAMPLE 2

Preparation of a Cement Ca/P=1.546; L/S=0.45; NaGP=0%

The proposed preparation corresponds to a preparation for a final quantity of 145 g.

a) There is first prepared a powder mixture of exact weight comprising the following constituents:
Tetracalcium phosphates=16.8 g. The tetracalcium phosphate is ground such that its granulometry is less than 70 micron.
α tricalcium phosphates=83.3 g, such that the calcium/phosphorous atomic ratio of this mixture will be equal to 1.573.
This mixture is carefully homogenized by means of a powder mixture.

There is then prepared a solution in the following manner:
b) 1.67 g (1 ml) of concentrated phosphoric acid is measured out (d=1.69); there is slowly added 0.40 g of calcium hydroxide. The mixture is brought up to 45 ml with distilled water. There is thus obtained a clear solution, stable in its calcium/phosphorus atomic ratio Ca/P=0.378.

c) There is poured into a small mortar the mixture of powder. There is then added all of the solution while energetically mixing by means of a pestle or a spatula. The mixture is initially granular but very quickly becomes smooth and homogeneous. After about one to two minutes of mixing, the mixture is left to stand. After about 25 minutes there is a consistency such that it can be molded in place. Its setting up is complete after about 35 minutes.

The cement prepared according to this second method has an overall atomic ratio Ca/P=1.546 and a liquid/solid ratio L/S=0.45.

In the case of this cement, the limit value (250 g/mm$^2$) is reached after 30 minutes. The resistance to compression is 8 Mpa. Its porosity is 45%.

EXAMPLE 3

Ca/P=1.63; L/S=0.42; NaGP=4.5%

The following cement is prepared as the previous ones. The composition of the different portions is:
Solid pulverulent phase:
Tetracalcium phosphate 16.8 g.
α tricalcium phosphate=83.3 g.
Sodium glycerophosphate (NaGP)=65 g such that the atomic ratio of calcium/phosphor of this mixture will be equal to 1.76.
Liquid phase:
Phosphoric acid (d=1.69)=2.47 g.
Calcium hydroxide=1.50 g.
Made up to 43 cm$^3$ with distilled water.
The atomic ratio of the liquid is 0.367.
After this mixing, the paste sets up in 15 minutes. It final hardness is 20 Mpa.

EXAMPLE 4

Ca/P=1.67; L/S=0.43; NaGP=9%

The following cement is prepared as above. The composition of the different parts is:
Pulverulent solid phase:
Tetracalcium phosphate=49.0 g.
α tricalcium phosphate=37.8 g.
Sodium glycerophosphate (NaGP)=130 g such that the calcium/phosphate atomic ratio of this mixture will be equal to 1.76.
Liquid phase:
Phosphoric acid (d=1.69)=1.0 g
Calcium hydroxide=1.44 g made up to 43 cm$^3$ with distilled water.
The atomic ratio of the liquid is 0.367.
After mixing, the paste sets up in 15 minutes. Its final hardness is 20 Mpa. Its porosity is 40%.

EXAMPLE 5

Ca/P=1.58; L/S=0.45; NaGP 9%; Ca/P=1.546; L/S 0.45; NaGP=0%

The following cement is prepared as the previous ones. The different composition of the portions is:
Solid pulverulent phase:
Tetracalcium phosphate=49.0 g
α tricalcium phosphate=62.0 g.
Sodium glycerophosphate (NaGP)=13 g such that the calcium/phosphorus ratio of this mixture will be equal to 1.727.
Liquid phase:
Phosphoric acid (d=1.99)=0.6 ml.

Calcium hydroxide=1.44 g made up to 43 ml with distilled water.

The atomic ratio of the liquid is 0.377.

After mixing, the paste sets up in 20 minutes. Its final hardness is 10 Mpa. Its porosity is 48%.

EXAMPLE 6

There is industrially prepared in the following manner quantities of 2 kg of powder and 1000 cm$^3$ of solution containing respectively:

Solid pulverulent product:
Tetracalcium phosphate=980 g.
α tricalcium phosphate=758.0 g
Glycerophosphate=260 g.
Solution:
Calcium hydroxide=34.0 g.
Phosphoric acid (d=1.69)=138 g.
Completed to 1000 cm$^3$.

From these products are prepared surgical sets containing: 11.6 g of pulverulent solid in a bottle having 5 cm$^3$ (that is 5.8 g) of solution in a sealed ampule. The whole is placed in a cardboard box, reference and sterilized by ionizing radiation.

From these products are prepared dental sets containing: 1.0 g of solid pulverulent in a closed bottle and 0.5 cm$^3$ of solution in a sealed ampule.

EXAMPLE 7

Preparation of a Cement Containing Chitosan, such that: Ca/P=1.63; L/S=0.43; NaGP=9%; Chitosan 0.5%

The cement is prepared as before, the compositions of different portions are as follows:

Solid
Tetracalcium phosphate: 49.0 g
α tricalcium phosphate: 37.9 g
Sodium glycerophosphate: 13 g
Solution
Calcium hydroxide: 3.4 g
Phosphoric acid (d: 1.69)=13.8 g
Chitosan (Deacelated to 50%)=1 g
Completed to 100 ml 11.6 g of pulverulent solid are mixed with 5 ml of the solution. The whole is ground for 1 minute. After a duration of 15 minutes, the cement has sufficient hardness to be emplaced in a surgical site; however, its setting up is not complete until after 1 hour.

When hardening is carried out under moist conditions analogous to those in a biological medium, the cement after one full day of development has a crushing strength equal to 20 Mpa.

X ray diffraction carried out after 24 hours and after one week, show that the evolution toward the apatite phase is not total. A portion of the cement has evolved toward a pre-apatite phase of the octocalcium phosphate type.

What is claimed is:

1. A process for the preparation of a biomaterial comprising a hardening phase at a utilization site, in which calcium phosphates are mixed to obtain a hydroxy apatite with an atomic ratio Ca/P of between 1.50 and 1.67, the process comprising the steps of:
   (a) mixing a tricalcium phosphate powder and a tetracalcium phosphate powder to obtain a solid pulverulent product having an atomic ratio Ca/P of between 1.40 and 1.90;
   (b) preparing an aqueous solution or solutions containing calcium ions and phosphate ions having an overall atomic ratio Ca/P of the solutions greater than 0.20 and the atomic ratio Ca/P of each solution less than 0.50; and
   (c) mixing the aqueous solution or solutions, the solid pulverulent product and optionally water to obtain a final mixture with a liquid/solid weight ratio of between 0.30 and 0.65 so as to obtain a homogeneous paste of an atomic ratio Ca/P of between 1.50 and 1.67, the paste being emplaced at the utilization site for in situ hardening.

2. The process according to claim 1, wherein a batch of the solid pulverulent product is obtained from step (a), a batch of an aqueous solution containing both calcium ions and phosphate ions is prepared from step (b), the batches of solid product and of aqueous solution having an overall liquid/solid weight ratio of between 0.30 and 0.65 and an overall atomic ratio Ca/P of between 1.50 and 1.67, and in step (c) the batch of solid pulverulent product and the batch of aqueous solution are mixed homogeneously without the addition of water.

3. The process according to claim 1, wherein the solid pulverulent product from step (a) has a mean diameter of the grains D50 of between 15 and 50 microns and a cutting diameter D95 equal to 100 microns.

4. The process according to claim 1, wherein the tricalcium phosphate powder comprises α tricalcium phosphate powder.

5. The process according to claim 1, wherein the aqueous solution is prepared by mixing in water, phosphoric acid with at least one of calcium hydroxide and calcium carbonate.

6. The process according to claim 1, further comprising lowering the pH of the aqueous solution by adding a small quantity of acid with the pH of the solution remaining greater than 1.

7. The process according to claim 1, wherein the solid pulverulent product has an atomic ratio Ca/P of between 1.70 and 1.85 and the aqueous solution has an atomic ratio Ca/P of between 0.35 and 0.40.

8. The process according to claim 1, further comprising adding a glycerophosphate to at least one of the solid pulverulent product and the aqueous solution, the weight percentage of the glycerophosphate in the final mixture being less than 15%
   wherein said glycerophospate is added in a manner so that the final atomic ratio of Ca/P is between 1.50 and 1.67 and the liquid/solid weight ratio is between 0.30 and 0.65.

9. The process according to claim 1, further comprising adding lactic acid to at least one of the solid pulverulent product and the aqueous solution, the weight percent of the lactic acid in the final mixture being less than 4%.

10. The process according to claim 1, further comprising adding at least one element selected from the group consisting of an alginate, guar gum and chitosan to at least one of the solid pulverulent product and the aqueous solution, the weight percentage of the elements in the final mixture being less than 2%.

11. The process according to claim 1, further comprising adding an active substance selected from the group consisting of an antibiotic substance, an antimitotic substance and a growth factor substance to the solid pulverulent product.

12. The process according to claim 1, wherein step (c) is performed at ambient temperature, the mixture hardening at a temperature below 40° C.

13. The process according to claim 1, wherein to produce by molding a piece for surgical or prosthetic use, step (c) is performed at ambient temperature;

depositing the mixture in a mold at ambient temperature to obtain a piece; and removing the piece from the mold and heating the piece to a temperature between 50° C. and 90° C. in a moist or aqueous atmosphere to obtain complete hardening.

14. Surgical or dental set, comprising:

a first batch of a solid pulverulent product comprising a mixture of tricalcium phosphate and tetracalcium phosphate with an atomic ratio Ca/P of between 1.40 and 1.90, the first batch packaged in a first closed sterilized container; and a second batch of an aqueous solution containing calcium ions and phosphate ions with an atomic ratio Ca/P of between 0.20 and 0.50, the second batch being packaged in a second closed sterilized container;

the first and second batches having an overall liquid/solid weight ratio of between 0.30 and 0.65 and an overall atomic ratio Ca/P of between 1.50 and 1.67.

15. The surgical or dental set according to claim 14, wherein the first batch contains a weight percent of sodium, potassium or calcium glycerophosphate of between 5 and 15% wherein said glycerophospate is added in a manner so that the final atomic ratio of Ca/P is between 1.50 and 1.67 and the liquid/solid weight ratio is between 0.30 and 0.65.

* * * * *